(12) United States Patent
Jacobs et al.

(10) Patent No.: US 6,848,905 B2
(45) Date of Patent: Feb. 1, 2005

(54) METHOD OF MAKING A DENTAL TRAY USING A PATIENT'S TEETH AS A TEMPLATE

(75) Inventors: Scott Jacobs, Golden, CO (US); Scot N. Andersen, Draper, UT (US)

(73) Assignee: Archtek, Inc., Lakewood, CO (US)

( * ) Notice: Subject to any disclaimer, the term of this patent is extended or adjusted under 35 U.S.C. 154(b) by 163 days.

(21) Appl. No.: 10/224,700

(22) Filed: Aug. 20, 2002

(65) Prior Publication Data

US 2004/0038171 A1 Feb. 26, 2004

(51) Int. Cl.$^7$ .................................................. A61C 9/00
(52) U.S. Cl. ........................................................ 433/37
(58) Field of Search .......................... 433/37, 48, 213, 433/214; 128/859, 861

(56) References Cited

U.S. PATENT DOCUMENTS

| | | |
|---|---|---|
| 1,663,695 A | 3/1928 | Foster, Jr. |
| 3,224,441 A | 12/1965 | Monaghan |
| 3,312,218 A | 4/1967 | Jacobs |
| 3,838,513 A | 10/1974 | Katz et al. |
| 4,033,774 A | 7/1977 | Johnson et al. |
| 4,044,762 A | 8/1977 | Jacobs |
| 4,073,061 A * | 2/1978 | Bergersen .................... 433/6 |
| 4,082,693 A | 4/1978 | Kessler et al. |
| 4,173,505 A | 11/1979 | Jacobs |
| 4,361,528 A | 11/1982 | Ginsburg et al. |
| 4,370,133 A | 1/1983 | Stempel |
| 4,401,616 A | 8/1983 | Wagner |
| 4,413,979 A | 11/1983 | Ginsburg et al. |
| 4,569,342 A | 2/1986 | von Nostitz |
| 4,619,610 A | 10/1986 | Pelerin |
| 4,668,188 A | 5/1987 | Wolfenson et al. |
| 4,672,081 A | 6/1987 | Fisher et al. |
| 4,776,792 A | 10/1988 | Wagner et al. |

(List continued on next page.)

FOREIGN PATENT DOCUMENTS

| | | |
|---|---|---|
| DE | 4011204 A1 | 10/1990 |
| JP | 406038988 A | 2/1994 |
| WO | WO 91/12777 | 9/1991 |

Primary Examiner—Melba Bumgarner
(74) Attorney, Agent, or Firm—Workman Nydegger

(57) ABSTRACT

A customized dental tray comprising ULDPE is formed using a person's own teeth as a template, or using a stone model of the person's teeth. A preformed dental tray or sheet comprising ULDPE is heated to become plastically deformable and placed over at least a portion of the person's teeth in order to form an impression of the person's teeth and yield an intermediate customized dental tray. Upon cooling sufficiently, the intermediate tray is removed from the persons' mouth and trimmed as needed to yield a finished customized tray corresponding to the person's teeth. The performed tray or sheet preferably comprises ULDPE, which yields a highly flexible and resilient final tray, although they may also contain other polymers or blends. The customized dental tray is useful for teeth bleaching and other dental treatments known in the art.

35 Claims, 8 Drawing Sheets

U.S. PATENT DOCUMENTS

| | | |
|---|---|---|
| 4,867,680 A | 9/1989 | Hare et al. |
| 5,051,476 A | 9/1991 | Uji et al. |
| 5,066,231 A | 11/1991 | Oxman et al. |
| 5,067,896 A * | 11/1991 | Korn ............................ 433/6 |
| 5,112,225 A | 5/1992 | Diesso |
| 5,213,498 A | 5/1993 | Pelerin |
| 5,415,544 A | 5/1995 | Oxman et al. |
| 5,503,552 A | 4/1996 | Diesso |
| 5,548,848 A | 8/1996 | Huybrechts |
| 5,562,449 A | 10/1996 | Jacobs et al. |
| 5,582,517 A | 12/1996 | Adell |
| 5,591,786 A | 1/1997 | Oxman et al. |
| 5,616,027 A | 4/1997 | Jacobs et al. |
| 5,769,633 A | 6/1998 | Jacobs et al. |
| 5,807,100 A | 9/1998 | Thornton |
| 5,829,441 A | 11/1998 | Kidd et al. |
| 5,924,863 A | 7/1999 | Jacobs et al. |
| 5,993,208 A | 11/1999 | Jonjic |
| 6,012,919 A | 1/2000 | Cross, III et al. |
| 6,017,217 A | 1/2000 | Wittrock |
| 6,089,869 A | 7/2000 | Schwartz |
| 6,126,443 A | 10/2000 | Burgio |
| 6,142,780 A | 11/2000 | Burgio |
| 6,183,251 B1 | 2/2001 | Fisher |
| 6,196,840 B1 | 3/2001 | Zentz et al. |
| 6,244,864 B1 | 6/2001 | Fujiwara et al. |
| 6,257,239 B1 | 7/2001 | Kittelsen et al. |
| 6,322,360 B1 | 11/2001 | Burgio |
| 6,364,665 B1 | 4/2002 | Trettenero |
| 6,581,604 B2 * | 6/2003 | Cook ........................ 128/859 |

* cited by examiner

METHOD OF MAKING A DENTAL TRAY USING A PATIENT'S TEETH AS A TEMPLATE

BACKGROUND OF THE INVENTION

1. The Field of the Invention

The present invention is in the field of customized dental trays used to provide a desired dental treatment to a person's teeth. More particularly, the invention relates to customized dental trays that are formed using either a person's teeth or a stone model of the person's teeth as a template. The tray can be used for dental treatments such as bleaching, administration of fluoride, or application of other medicines.

2. The Relevant Technology

Virtually all people desire white or whiter teeth. To achieve this goal, people either have veneers placed over their teeth or have their teeth chemically bleached. In the past, patients who desired to have their teeth bleached had to submit to conventional in-office bleaching techniques. The process generally involves: (1) making an alginate impression of the patient's teeth; (2) making a stone cast or model of the impression; (3) vacuum forming a dental tray from the model, usually from a sheet of thin ethyl vinyl acetate (EVA) material, and trimming to exclude gingival coverage. This method results in a tray that is soft and flexible, that is very accurately customized to the patient's teeth, but the method is time consuming and the resulting tray is expensive.

Because of the high cost of these very accurate custom trays, less costly alternatives have been developed, but these alternatives have substantial disadvantages in terms of accuracy and comfort of the finished formed tray.

One alternative is the so-called "boil and bite" tray. A relatively thick, non-custom preformed tray (similar to a mouth guard) made of EVA or polyethylene or other material is submerged in boiling water. Upon removal from the water, the tray is quickly placed inside the patient's mouth. The patient quickly applies contact pressure to make an impression of the biting surfaces of the user's teeth. One problem with "boil and bite" trays is that they are relatively thick and bulky, which make them intrusive and uncomfortable to wear. The thickness of large, bulky perform trays also limits the accuracy with which they can conform to the user's teeth and/or gums.

To the extent that preform trays made from EVA and like materials are made with thinner walls, such trays are extremely difficult to work with because they tend to shrivel and collapse outside extremely narrow windows of temperature and heating time. For example, if left in a hot water bath too long (i.e., for more than a few seconds) they can quickly become limp and lose their pre-form shape, making it difficult or impossible to make an impression of the user's teeth. In view of the foregoing, "boil and bite" trays that do not have the tendency to collapse and shrivel when heated generally do not accurately conform to the user's teeth and are bulky and uncomfortable to wear.

Another alternative for teeth bleaching involves non-customized strips of a flexible plastic material coated with a bleaching agent that can be applied to the teeth. Such strips are placed against the teeth by the user to cover the teeth. Because such strips are flimsy and limp at room temperature (i.e., are not resilient or rigid), they are not useful for creating a customized dental tray.

Another alternative is a dual tray assembly as disclosed in U.S. Pat. No. 5,616,027 to Jacobs et al. The dual tray assembly is composed of an outer tray that supports or carries an inner tray made of a thermoplastic material comprising EVA. In use, the tray assembly is submerged in hot water, where the inner tray becomes pliable and moldable and the outer tray remains rigid. "Because of the material and the thinness of the walls of the inner tray, the inner tray will substantially lose integrity of its shape and form during the heating process . . . . " (Col. 4, ll. 14–16.) Thus, "[t]he carrier tray is necessary during the heating, handling and forming process." (Col. 4, ll. 16–17.) The heated assembly is then placed in the mouth of the patient where the inner tray takes an impression of the person's teeth. The generally thinner inner tray results in a final tray that is much thinner and more comfortable to wear compared to conventional "boil and bite" trays that are sufficiently thick that they do not need a supporting carrier tray. Nevertheless, the outer tray can inhibit accurate conformation of the inner tray to the shape of the patient's teeth.

Another problem with EVA are concerns about its toxicity. Whereas trays made using EVA are generally safe to use, the FDA has guidelines that strictly controls how EVA can be used. Notwithstanding the foregoing deficiencies, EVA finds wide use in the manufacture of dental trays, which is strong evidence of the inadequacy of other possible plastic materials that are suggested in various existing patents relating to tray technology. EVA is generally preferred due to its softness and flexibility and the ease in which it can be heated and formed into a dental tray compared to other plastic materials suggested in the art.

In view of the foregoing, there is an ongoing need to develop new materials for use in manufacturing preformed trays and sheets that can be easily formed into customized trays that are thin-walled, flexible, comfortable, and that accurately reflect the shape of the person's teeth.

SUMMARY OF THE INVENTION

The present invention is directed to customized dental trays that in one aspect are formed by using a person's own teeth as a template. In this case, a preformed tray or sheet is heated to a point where it is sufficiently softened that it can be plastically molded so as to conform to the person's teeth. Upon cooling, the customized tray retains its shape so that it can be used repeatedly as needed to provide a dental treatment. In another aspect, preformed trays or sheets comprising ultra low density polyethylene are formed into customized trays using a stone or plaster model of the person's teeth.

The process for making a finished customized tray begins with a preformed dental tray or flat sheet that may optionally be available in multiple sizes to allow the selection of a size that generally conforms to the size of the person's teeth and mouth. The tray or sheet preferably comprises ultra low density polyethylene ("ULDPE"), either alone or blended with one or more additional polymers, e.g., ethylene-vinyl acetate copolymer ("EVA"), ε-polycaprolactone ("PCL"), other types of polyethylene ("PE"), polypropylene ("PE"), or other plastic materials. Plasticizers or flow additives known in the thermoplastic art can be used as desired to modify the properties of the thermoplastic material used to form the preformed dental tray or sheet.

Preformed trays and sheets made from ULDPE are preferred due to the unique ability of trays and sheets made therefrom to soften and yet maintain their physical integrity while in a softened state compared to previous tray or sheet materials such as EVA. Thus, ULDPE expands the operational window, both in terms of temperature and heating time, of manufacturing customized dental trays compared to previous tray materials. In other words, preformed trays and sheets made from ULDPE are far less susceptible to over or under heating compared to trays or sheets made from EVA. Even though preformed trays and sheets made from ULDPE do not shrink or otherwise lose their physical integrity when heated as happens using trays or sheets made from EVA, they do, in fact, shrink over and around and cling to the person's teeth (or a stone cast of the person's teeth) when cooling, which greatly simplifies and improves the ability of such trays or sheets to accurately conform to the person's teeth (or stone cast). Moreover, ULDPE is non-toxic, thereby addressing any potential concerns with the toxicity of EVA, while providing the aforementioned superior physical and/or mechanical properties. These demonstrate the surprising and unexpected benefits of using preformed trays or sheets comprising ULDPE compared to trays materials considered at present to be the industry standard (i.e., trays comprising EVA).

The outer configuration of the preformed dental tray is preferably a horseshoe shape, with a flat planar bottom having an open U-shaped cross-section to generally fit over the upper and/or lower teeth. The walls of the preformed tray may be either parallel or flared, the latter providing a larger top opening than the width of the tray bottom. The tray advantageously includes a handle, preferably attached at the front lower portion of the tray.

The tray or sheet is advantageously designed and formulated so as to soften when heated to a desired temperature above body temperature (i.e. 98.6° F.), preferably in a range of about 110° to about 180° F., more preferably in a range of about 120° to about 170° F., and most preferably in a range of about 130° to about 160° F. Upon heating to an appropriate temperature at or above its softening temperature, the tray or sheet becomes plastically deformable and moldable so that it can form an impression of the teeth or teeth and gums.

The tray customization process is done by immersing the preformed tray or sheet into hot water or by other exposing it to other suitable heating means known in the art (e.g., heat gun, oven or torch). A handle can be used to facilitate immersion of the tray in hot water or heating using other means while reducing the risk of burning one's fingers. The tray or sheet will typically become plastically deformable after being submerged within water heated to a temperature of about 160–212° F. or heated using other appropriate heating means within a prescribed period of time, preferably within about 1–30 seconds, more preferably within about 2–15 seconds, and most preferably within about 4–8 seconds.

When sufficiently softened and plastically deformable, the tray or sheet is placed over the person's upper and/or lower teeth and the person closes his or her mouth. A vacuum is advantageously created inside the tray by the patient sucking in a manner so as to draw air and/or water out from the space between the tray and tooth surfaces. Additional forming pressure can be applied by the person's tongue or by placing the patient's or dental practitioner's fingers against the outer surfaces of the tray. Nevertheless, due to the aforementioned benefit of preformed trays or sheets comprising ULDPE to shrink and cling against and around the person's teeth when they begin to cool, less mechanical force is needed to cause the trays or sheets to adequately and accurately conform to the person's teeth (or a stone model) compared to other tray materials known in the art.

As the tray remains in the person's mouth it begins to cool to body temperature. After the customized tray has been formed and cooled sufficiently so that it is no longer plastically deformable, it is removed from the person's mouth. The tray may be further cooled if desired, such as by placing the tray in cold water or by letting it air cool to room temperature. The formed tray will have an impression of the teeth and is therefore a "custom" or "customized" tray. Upon cooling, the tray may remain flexible and resilient but it will not be "plastically deformable" so as to assume a different resting conformation unless reheated and reshaped. If additional shaping is needed, either immediately or later, the tray may be heated and customized as before.

Once the customization process is complete, the detachable handle can be removed by e.g., cutting or tearing. The customized tray is preferably trimmed to or shy of the gingival margin of the frontal and/or lingual surfaces. The tray is preferably scalloped in around the interdental papilla in order to produce maximum customization and comfort. Nevertheless, the tray can be trimmed to cover a portion of the teeth, just the teeth, or to cover a portion of the gingiva in addition to the teeth, as desired.

The customized trays formed in this manner are useful for tooth bleaching or other dental treatments. Bleaching or other dental compositions can be applied to a person's teeth and/or gums by placing the composition into the customized tray and placing the tray over the person's teeth. The tray holds the dental composition against the person's teeth and/or gums and keeps it from being diluted by saliva or otherwise being prematurely removed. In a preferred embodiment, the dental composition may include an appropriate tackifying agent in order to make it sticky and viscous. The tray can be used once or many times as desired to treat the person's teeth and/or gums.

In some cases, it may be desirable to incorporate reservoirs within the customized tray. Reservoirs can enhance treatment of the teeth or other tissue by holding additional treatment material adjacent to the dental tissue(s) being treated. To form tray reservoirs, an appropriate blockout material, such as clay, wax, a light or chemical cure resin, or other suitable coating material may be placed over one or more of the person's teeth and/or gingival tissue. The blockout material displaces the perform tray or sheet material away from the teeth by a distance corresponding to the thickness of the blockout material, which results in the creation of reservoirs within the customized tray. After tray formation, the blockout material is removed from the person's teeth and/or gingival tissue.

Whereas preformed trays and sheets are especially useful for manufacturing customized dental trays using a person's teeth, rather than a stone cast, as the template, it is certainly within the scope of the invention to vacuum form preformed trays or sheets made from ULDPE using a stone cast. An advantage of using preformed trays or sheets that comprise ULDPE using conventional tray-making methods that employ a stone cast is that such trays or sheets, by virtue of their including ULDPE, can be made thinner than preformed trays or sheets using conventional tray-making materials. In this way it is possible to manufacture final customized trays that are even thinner walled and more flexible than conventional trays. This is a surprising and unexpected result.

Moreover, ULDPE is more transparent or translucent than conventional tray materials, which increases the ability to determine whether the dental composition is sufficiently well distributed so as to cover the desired tooth and or gingival surfaces. This is yet another surprising and unexpected result of employing tray materials that comprise ULDPE.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

In one aspect, the invention relates to the manufacture of customized dental trays using a person's own teeth as the template. In another aspect, the invention relates to the use of preformed trays or sheets that comprise ULDPE in making customized dental trays, either using a person's teeth or a stone cast of the person's teeth as a template. In another aspect, the invention relates to customized dental trays that comprises ULDPE. The inventive dental trays can be used for any desired dental treatment, such as tooth bleaching, fluoride treatments, and antimicrobial treatments. Reference is now made to the drawings.

Figure 1:
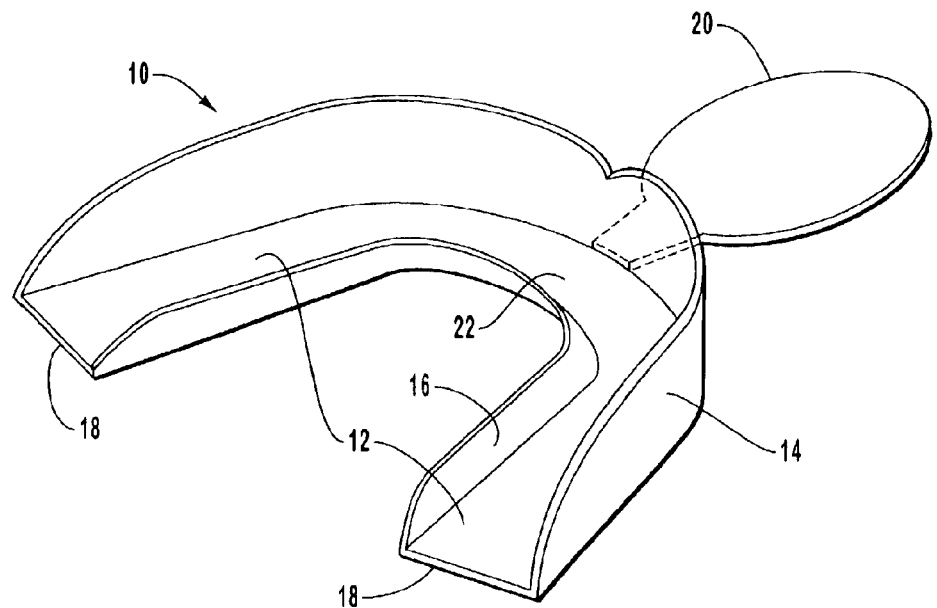
FIG. 1 is a perspective view illustrating an embodiment of a preformed dental tray according to the invention that can be used to form a customize dental tray.

FIG. 1 depicts a preformed dental tray 10 that may be used to manufacture a customized dental tray according to the invention. The preformed tray 10 comprises a bottom wall 12 having a generally U-shaped configuration generally conforming to the shape of the person's dental arch. The bottom wall 12 has a generally flat planar profile, although it could have other shapes if desired (e.g., curved). The preformed tray 10 further includes a front side wall 14 and a rear side wall 16 that, together with the bottom wall 12, form a tray 10 that is open at the top and that terminates at ends 18. A detachable handle 20 is attached to the tray 10 along an outer surface of the front side wall 14, preferably near the bottom center of the side wall 14. The interface between the detachable handle 20 and the front side wall 14 can be any desired length, preferably about 2–4 mm long, more preferably about 1/8 inch long (about 3.2 mm).

The front side wall 14 of the tray 10 is substantially perpendicular relative to the bottom wall 12. The rear side wall 16 of the tray 10 is substantially perpendicular to the bottom wall 12 at the ends 18 of the horseshoe-shaped tray 10, but gradually opens up to form an oblique angle near a middle curved portion 22 of the tray so as to better accommodate the roof of the mouth near the middle portion 22 of the tray 10. The bottom wall 12 has a width near the curved middle portion 22 of the tray that is advantageously less than the width of the bottom wall 12 between the middle portion 22 and the ends 18 of the tray 10. This allows for the differences in the radial width of a person's incisors and canines relative to the bicuspids and molars. It should be understood, however, that dental trays comprising ULDPE used within the scope of the invention can have any desired configuration such that the tray of FIG. 1 is merely a nonlimiting example.

The tray 10 can be made of any appropriate thermoplastic material that is able to soften at a predetermined temperature greater than body temperature so as to become plastically deformable but that will maintain its shape when cooled to at or below body temperature. A preferred thermoplastic material is ultra low density polyethylene (ULDPE), which can be used alone or in combination with other polymers, such as polypropylene (PP), ethylene vinyl acetate (EVA), polycaprolactone (PCL), and other forms of polyethylene (PE). Flow additives and plasticizers may be added as desired.

ULDPE is the preferred thermoplastic material because of its ability to maintain its structural form and integrity even after being heated sufficiently so as to become plastically deformable. Though they better maintain their shape and size during the heating process, preformed trays and sheets provide the unexpected and surprising benefit of shrinking and clinging against and around the person's teeth (or stone model of the person's teeth) upon cooling. This greatly aids in the ability and ease of tray materials comprising ULDPE to accurately and readily conform to the shape of the person's teeth (or stone model) compared to all (or virtually all) other tray materials known in the art. Moreover, customized trays that comprise ULDPE remain soft, flexible and resilient at room temperature. They are also more transparent or translucent than conventional tray materials. ULDPE reduces or eliminates the toxicity concerns of EVA, while providing superior mechanical properties. ULDPE helps in the ease of manufacture of the customized dental tray and it also maximizes patient comfort and compliance with the desired dental treatment.

ULDPE refers to a range of polyethylene-based copolymers defined as having a density of less than 0.914 g/cm$^3$. By way of comparison, low density polyethylene (LDPE) is defined as having a density in a range of 0.915–0.94 g/cm$^3$ and high density polyethylene (HDPE) is defined as having a density in a range of 0.94 to 0.97 g/cm$^3$. Thus, ULDPE can be readily distinguished from other forms of PE by its density, although its physical properties also differ significantly in many respects, including water vapor transmission rate, crystallinity, melting point, coefficient of linear expansion, elasticity, modulus, yield strength, tensile strength, hardness, and impact strength. In general, ULDPE is an ethylene copolymer characterized as having excellent environmental stress crack resistance, outstanding flex-life and flex-crack resistance, toughness and good sealability. It also has a relatively high melt flow index compared to conventional tray materials, which makes it uniquely suitable for use in manufacturing thin-walled customized dental trays. It has been found that, in general, the higher the melt flow index, the more the preformed trays or sheets made from the material will tend to maintain their shape after being heated to the material's softening temperature.

Examples of suitable ULDPE materials include various polymers sold under the general trade name Attane® by Dow Chemical. In general, Attane® refers to polyethylene copolymers made from ethylene and octene. Specific examples include Attane® 4201 (density=0.912 g/cm$^3$), Attane® 4202 (density=0.913 g/cm$^3$), Attane® 4203 (density=0.905 g/cm$^3$), Attane® 4301 (density=0.914 g/cm$^3$), and Attane® 4404 (density=0.904 g/cm$^3$). Another suitable ULDPE material is Exact(® 4041 (density=0.878 g/cm$^3$) made by Exxon-Mobil Chemical. An example of a suitable EVA material is Elvax® 250, available from Dupont. An example of a suitable PCL material is Capra® 650 from Solvoy-Interox. Other thermoplastic materials and blends used in making dental trays are disclosed in U.S. Pat. No. 5,769,633 to Jacobs et al., U.S. Pat. No. 5,051,476 to Uji et al., and U.S. Pat. No. 6,089,869 to Schwartz. For purposes of disclosing thermoplastic materials that can be made into customized dental trays, the foregoing patents are incorporated herein by reference.

Figure 2:
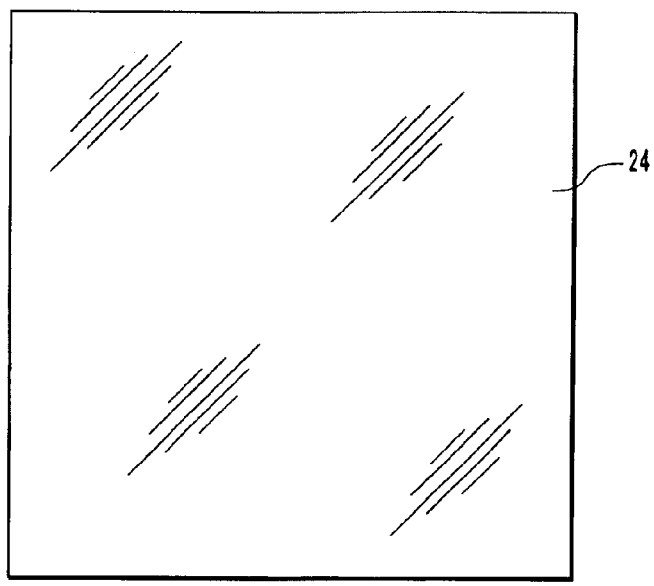
FIG. 2 is a perspective view illustrating a preformed sheet that may be used to form a customized dental tray according to the invention.

FIG. 2 depicts a generally flat preformed sheet 24 that may alternatively be used to form customized dental trays according to the inventive methods disclosed herein. The preformed sheet 24 preferably comprises ULDPE, either alone or blended with one or more additional polymers. The preformed sheet 24 is preferably a square having dimensions of about 5×5 inches, although other shapes and sizes are within the scope of the invention. For example, the preformed sheet may be cut into a generally horse-shoe shaped configuration (not shown) generally corresponding to the size and curvature of a person's dental arch.

In a preferred embodiment, the preformed tray 10 or sheet 24 become plastically deformable at a predetermined temperature in a range of about of about 110° to about 180° F., more preferably in a range of about 120° to about 170° F., and most preferably in a range of about 130° to about 160° F. The preformed tray 10 or sheet 24 preferably becomes plastically deformable after being immersed in water at temperature of about 160–212° F. (or by heating using other appropriate heating means) within about 1–30 seconds, more preferably within about 2–15 seconds, and most preferably within about 4–8 seconds.

The preformed tray 10 may advantageously be made available in a variety of sizes to accommodate varying sizes of teeth and/or dental arches. This aids tray forming and customization because a preformed tray that more closely fits the patient's mouth and teeth size can be selected. The preformed sheet 24 may likewise come in various sizes although it is more amenable to tray-forming methods that employ "one size fits all" approach than the preformed tray 10.

Figure 3A:
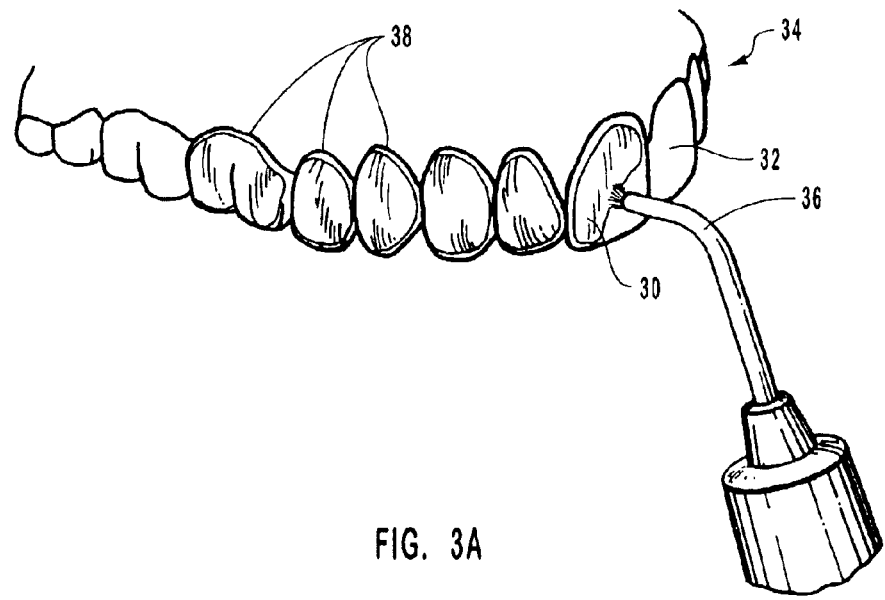
FIGS. 3A and 3B illustrate alternative methods of applying a blockout material to a person's teeth (or stone cast) in order to yield a customized dental tray having reservoirs.
Figure 3B:
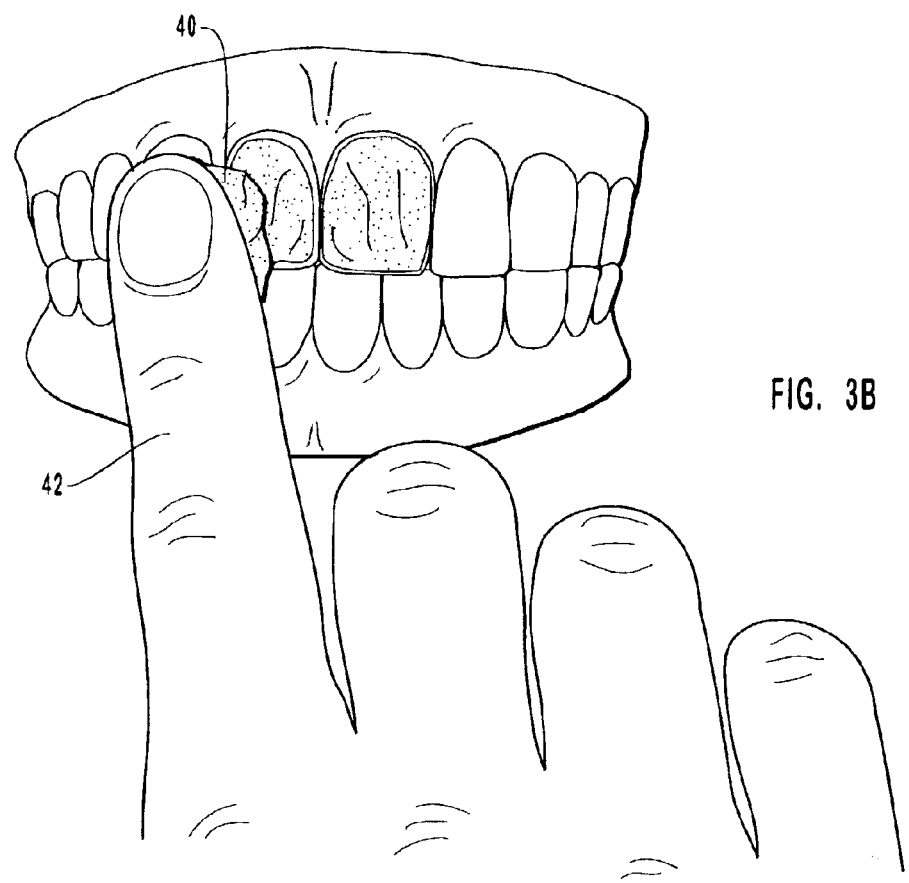

FIGS. 3A and 3B depict the optional use of a blockout material in order to yield a finished customized tray incorporating one or more reservoirs therein. Reservoirs may be desirable in order to provide additional dental composition adjacent to the teeth and/or gingival tissue being treated. Once a customized tray has been formed and then removed from the person's teeth, the blockout material is removed.

FIG. 3A depicts the application of a flowable blockout material 30 (e.g., a curable resin) onto the surfaces 32 of a person's teeth 34 (or stone cast) using a syringe tip 36 attached to a syringe (not shown). As shown therein, the flowable blockout material 30 may be applied to so as to substantially cover the tooth surfaces 32 just shy of the gingival margin 38, although it is certainly within the scope to cover the entire tooth surface and/or at least a portion of the gingiva if desired (or the portions of the stone cast representative of the person's tooth surfaces and gingival margin).

FIG. 3B depicts the application of a wax, clay or putty blockout material 40 by pressing it against the tooth surfaces (or stone cast) using a person's finger 42. Alternatively, highly viscous blockout materials or clays may be applied and/or excess blockout material may be removed using an application tool (not shown), such as a spatula.

The preformed tray 10 preferably has a composition and thickness so that when it is heated so as to become plastically deformable, the tray will tend not to collapse but will substantially retain its shape so that it can be readily molded into a customized dental tray. The benefit of using ULDPE is that ULDPE allows for the use of a thinner preformed tray or sheet compared to conventional tray materials.

In order to achieve the desired mechanical properties, both in the preformed tray and in the finished customized tray, the bottom wall 12 will preferably have a thickness of about 0.4 mm to about 2 mm, more preferably in a range of about 0.6 mm to about 1.5 mm, and most preferably in a range of about 0.8 mm to about 1.3 mm. The front side wall 14 and rear side wall 16 preferably have wall thicknesses in a range of about 0.3 mm to about 1.8 mm, more preferably in a range of about 0.4 mm to about 1.4 mm, and most preferably in a range of about 0.7 mm to about 1.2 mm.

When using a preformed sheet to manufacture the customized dental trays according to the invention, the preformed sheet will preferably have a thickness of about 0.4 mm to about 2 mm, more preferably in a range of about 0.6 mm to about 1.5 mm, and most preferably in a range of about 0.8 mm to about 1.3 mm.

Figure 4A:
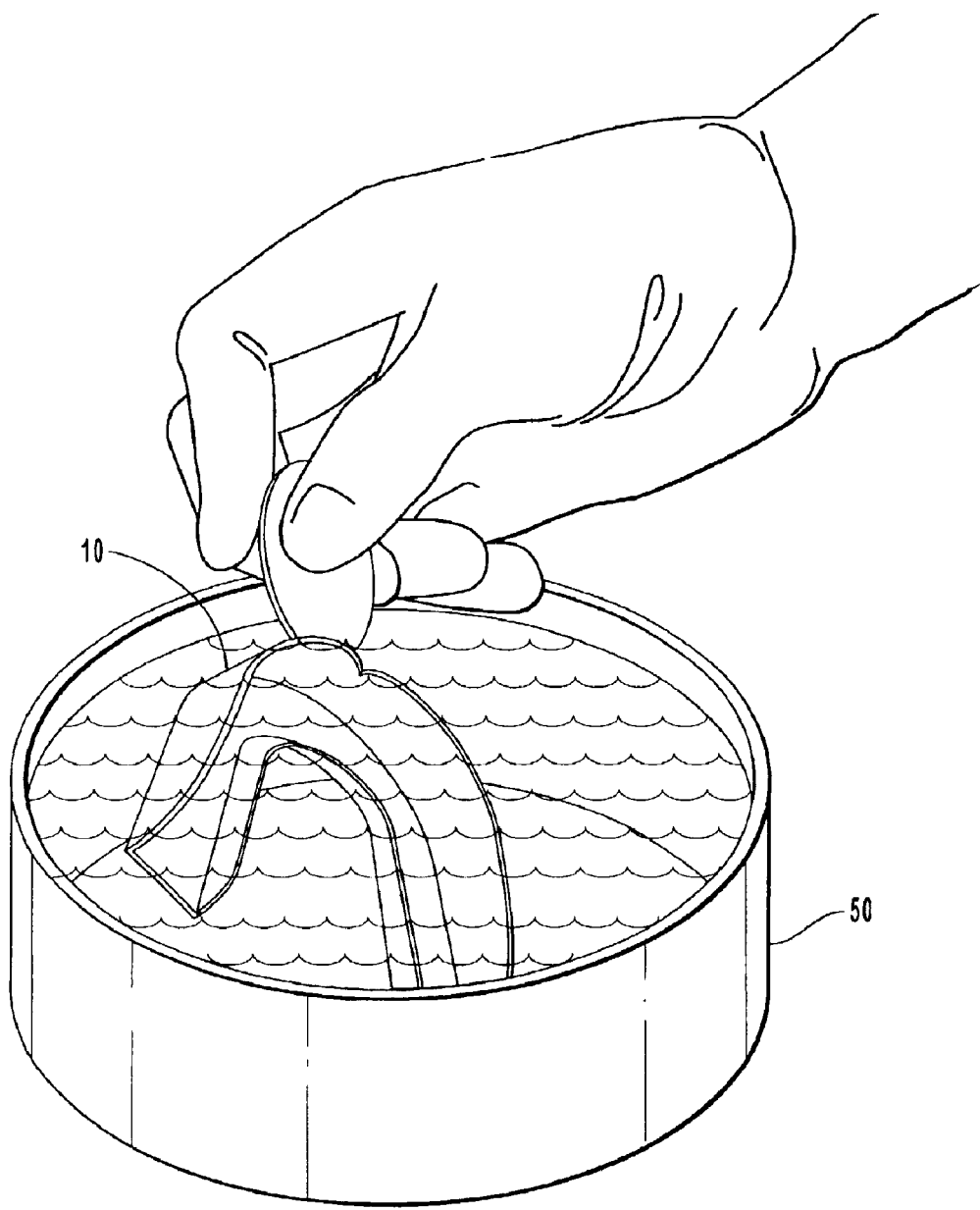
FIGS. 4A–4C illustrates alternative methods of heating a preformed tray in order to soften it preparatory to making a customized dental tray.
Figure 4B:
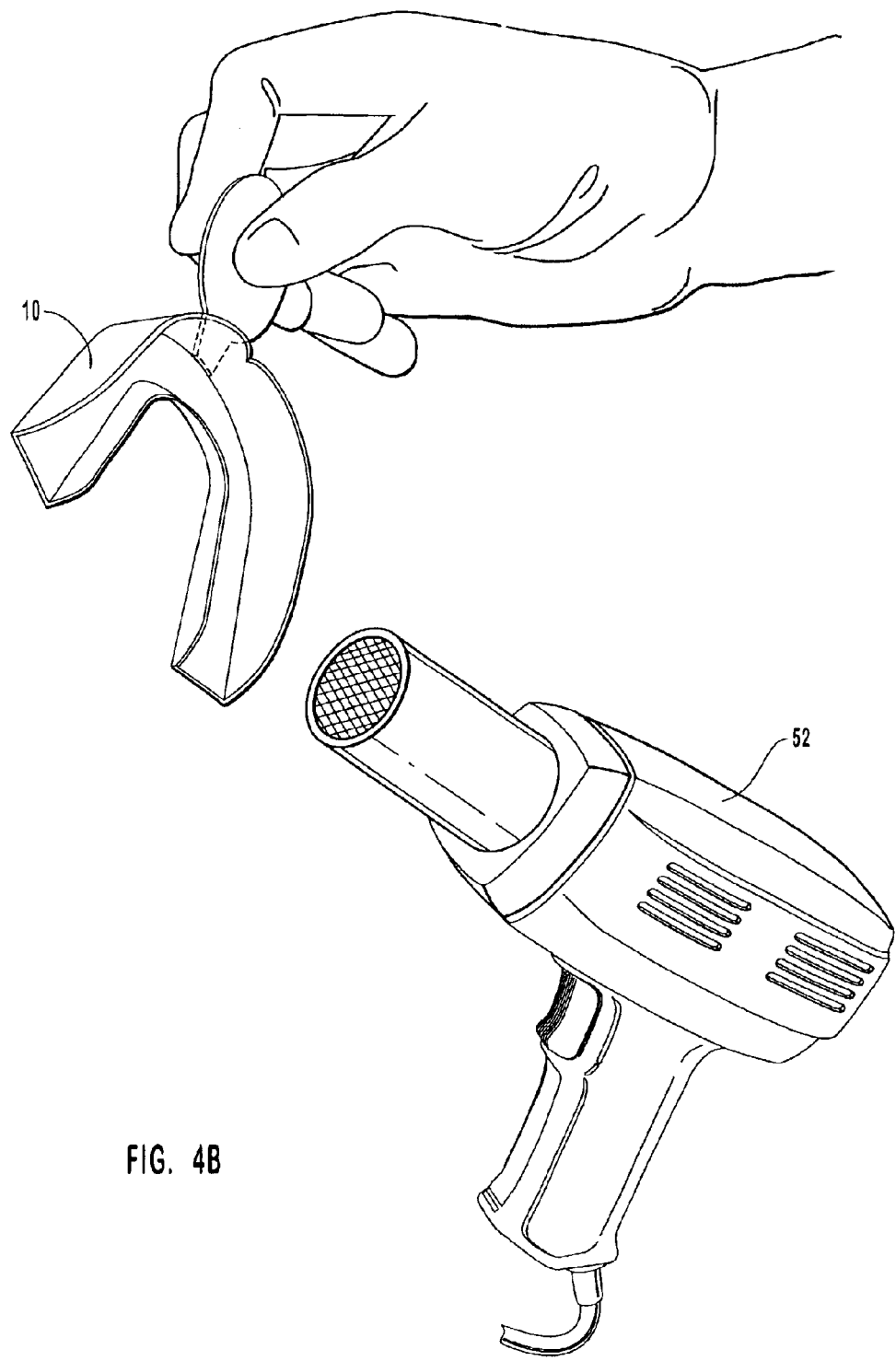
Figure 4C:
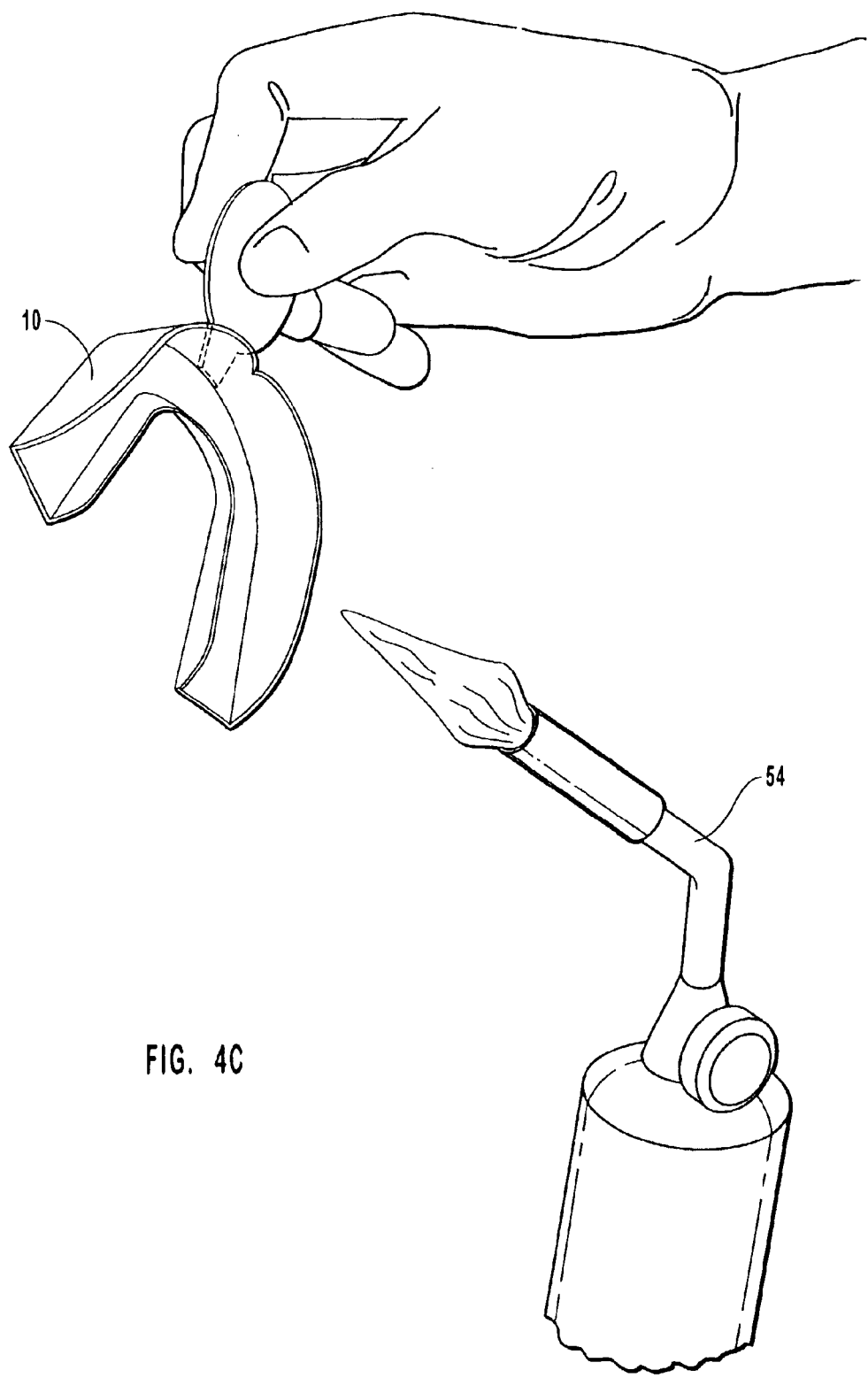

Reference is now made to FIGS. 4A–4C, which depict various methods for heating a preformed tray prior to forming the customized dental tray. FIG. 4A depicts a preformed tray 10 immersed in a bath 50 of hot or boiling water or other suitable liquid. The handle 20 allows the tray 10 to be submerged easily by the user and will advantageously remain outside the bath 50 as shown in FIG. 4A. This allows the tray 10 to be easily removed from the bath 50 after being heated to the desired temperature. In the alternative, the handle 20 may be submerged in the bath 50 along with the tray 10 and then grasped using a pair of tongues or other suitable gripping device (not shown) in order to remove the tray 10 from the bath 50.

FIG. 4B depicts the alternative use of a heat gun 52 to heat the preformed dental dray 10. FIG. 4C depicts the alternative use of a torch 54 to heat the preformed dental dray 10. When using these alternative h eat sources, care should be taken to heat the tray evenly, such as by moving the tray and/or heat source back and forth to avoid heating a single area to the exclusion of other areas.

Figure 5:
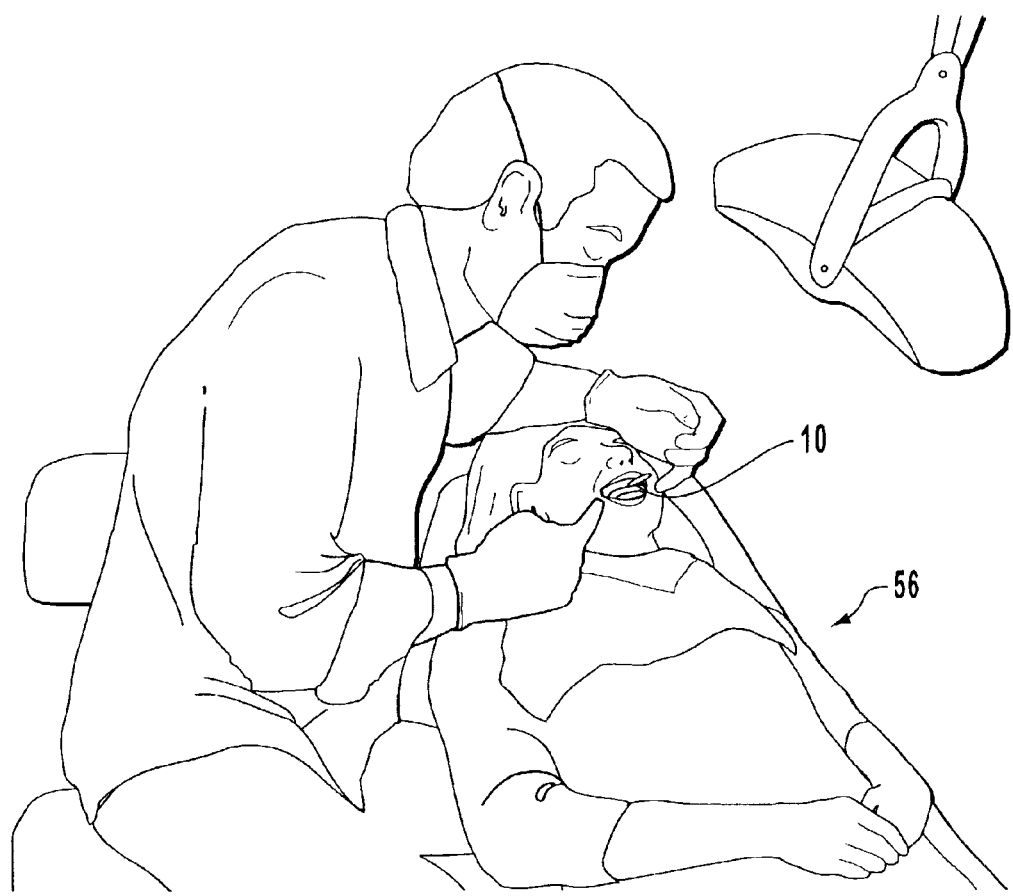
FIG. 5 illustrates the preformed dental tray of FIG. 1 being placed in a patient's mouth during formation of a custom-fitting tray using a person's teeth as a template.

Referring now to FIG. 5, after the tray 10 (or sheet 24, not shown) has been heated sufficiently so as to assume a plastically deformable condition, the tray 10 (or sheet 24, not shown) is inserted into the mouth of a person 56 (e.g., a patient) over the upper or lower teeth and the patient 56 closes his or her mouth. The preformed tray or sheet is plastically deformed (i.e., molded) so as to conform and correspond to at least a portion of the person's teeth. The person may assist this process by sucking and creating a vacuum within the person's mouth. This causes any water and/or air interposed between the person's teeth and tray material to be removed so that the tray material can more closely conform to the shape of the person's teeth. Additional forming pressure can be applied by the fingers of the person or the fingers of another assisting in the formation of the customized tray. The person may also use his or her tongue to press the tray material more closely against the lingual tooth surfaces. Nevertheless, due to the aforementioned benefit of preformed trays or sheets comprising ULDPE to shrink and cling against and around the person's teeth when they begin to cool, less mechanical force is needed to cause the trays or sheets to adequately and accurately conform to the person's teeth (or a stone model) compared to other tray materials known in the art.

After the preformed tray 10 (or preformed sheet 24) has been adapted so as to correspond to the person's teeth and has remained in the person's mouth for a significant period of time, it will naturally begin to cool. After the tray 10 (or sheet 24) has been customized so as to form an impression 58 within the intermediate customized tray 60 (FIGS. 6A and 6B) and is no longer plastically deformable, it is taken out of the mouth. It may be further cooled as desired, such as by placing the intermediate customized tray 60 in cold water or by letting it cool to room temperature. When cooled sufficiently, the impression 58 within the final customized tray 70 (FIG. 7) will become permanent. That is, the tray material can then be deformed to the extent that it is flexible and resilient but will return to its original customized shape upon removal of the deformation force. If additional plastic deformation is needed, either immediately or later, the customized trays 60, 70 may be heated so as to become plastically deformable, plastically deformed, and then cooled as describe above.

In the alternative, the intermediate customized tray 60 can be made by vacuum forming a preformed sheet that comprises UDLPE using conventional tray forming methods from a stone cast of a person's teeth. The preformed sheet 24 may be heated before or during vacuum formation as desired. The advantage of using a preformed sheet comprising UDLPE is that the final customized tray made therefrom can be thinner, more flexible, and more transparent compared to convention vacuum formed dental trays. It is also within the scope of the invention to form a customized dental tray from a preformed tray comprising UDLPE using a stone cast in order to obtain the same advantages.

In another embodiment, a preformed sheet 24 comprising ULDPE is placed over the person's teeth with the assistance of an auxiliary impression of the person's teeth. First, an impression of the person's teeth (not shown) is made using any suitable impression material (e.g., alginate or silicone). Second, the preformed sheet 24 is heated so as to become plastically deformable. Third, the heated preformed sheet 24 is placed over the impression of the person's teeth. Fourth, the preformed sheet 24 is placed over the person's teeth with the assistance of the impression in order to cause the sheet to conform to the person's teeth and form a customized tray. The impression assists in causing the preformed sheet to conform to the person's teeth.

Once the intermediate customized tray 60 has been formed using the preformed tray 10, the detachable handle 20 can be removed, such as by cutting or tearing. The customized trays 60, 70 may be sanded or otherwise smoothed in the area where the detachable handle 20 was cut or removed so as to remove any points or edges that might cause discomfort to the patient.

Figure 6A:
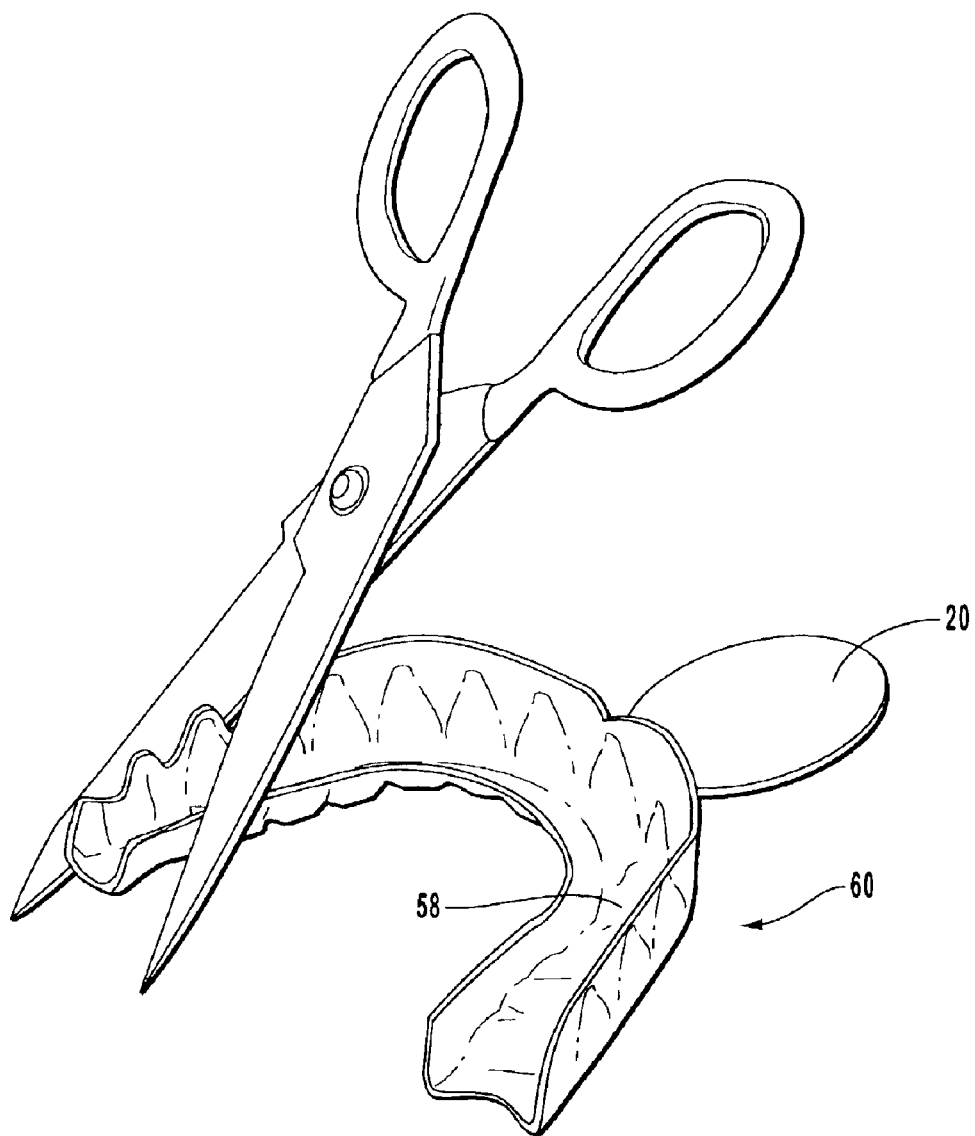
FIGS. 6A and 6B illustrate intermediate customized dental trays being trimmed in order to remove excess tray forming material.
Figure 6B:
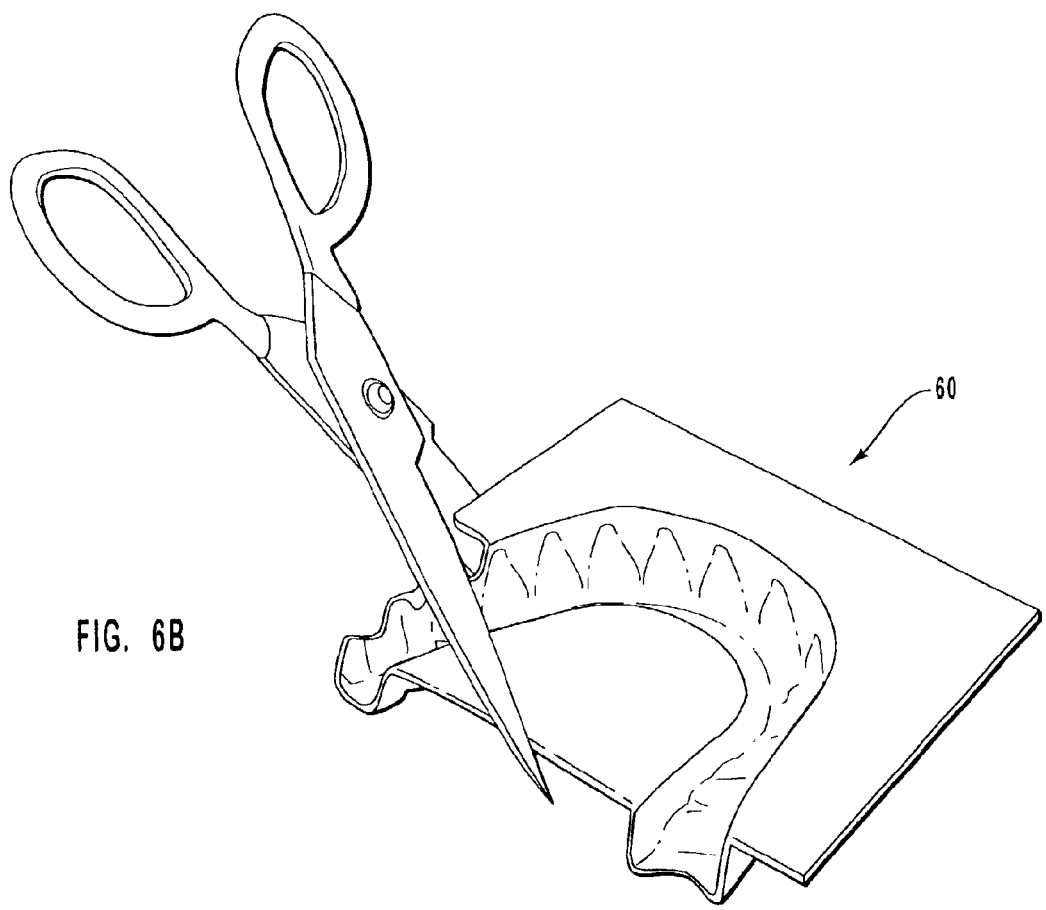
Figure 7:
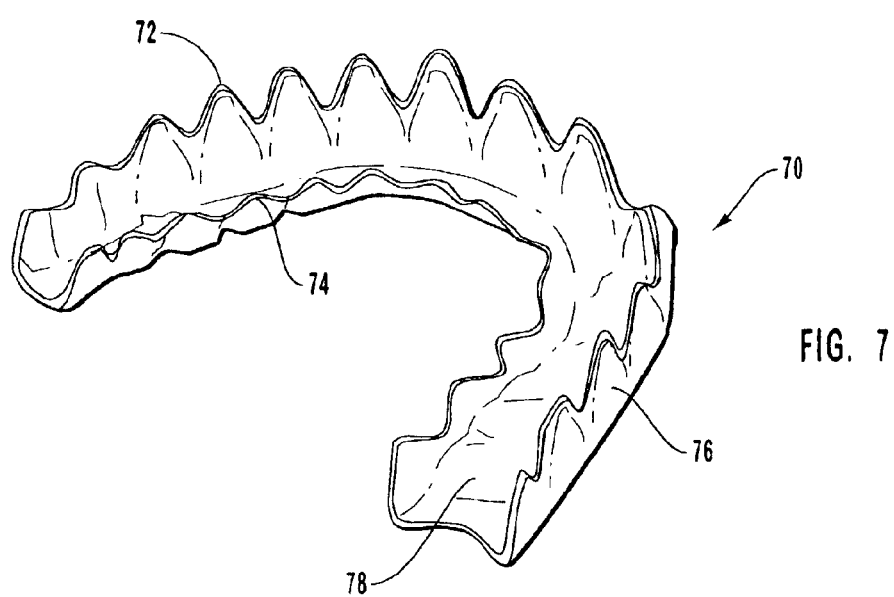
FIG. 7 illustrates a customized dental tray according to the invention that has been trimmed and scalloped.

As shown in FIGS. 6A and 6B, once formed, the intermediate customized tray 60 formed by whatever means can be trimmed as desired to yield a finished customized tray of a desired shape, such as to yield the finished tray 70 depicted in FIG. 7. In one embodiment, the customized dental tray can be trimmed so as to terminate at or shy of the gingival margin on both frontal and lingual surfaces. It may be desirable to scallop or trim the customized dental tray up and around interdental papilla so that the finished tray does not overlap them so as to achieve maximum patient comfort.

In general, the customized dental tray can be trimmed to cover a portion of the teeth just the teeth, or to cover a portion of the gingival margin in addition to the teeth. In one embodiment, it may be desirable to trim the customized dental tray so that enough tray material is left to assure that all of the tooth can be covered to within about ¼ mm to about ⅓ mm of the gingival margin.

As shown generally in FIG. 7, the finished tray 70 comprises a front upper periphery 72 that overlaps a desired portion of the person's frontal tooth surfaces, and optionally at least a portion of the gingival, when in use. The dental tray also includes a rear upper periphery 74 that overlaps a desired portion of the person's lingual tooth surfaces when in use. Together, the front upper periphery 72 and the rear upper periphery 74 comprise the "upper periphery" of the customized dental tray. The finished tray 70 further also includes a main body portion 76 having an impression 78 formed therein.

The customized dental trays made according to the invention can have any desired thickness. The customized trays wall preferably have an average wall thickness in a range of about 0.3 mm to about 1.8 mm, more preferably in a range of about 0.4 mm to about 1.4 mm, and most preferably in a range of about 0.7 mm to about 1.2 mm.

The finished customized dental trays according to the invention are useful for teeth bleaching or other dental treatments. In use, a desired dental composition is placed within the main body portion of the tray and the tray is placed over the person's teeth. The customized tray holds and maintains the dental composition against the person's teeth. The customized dental trays according to the invention can be used once or repeatedly as desired. Transparent trays made using UDLPE or blends thereof are both visually appealing and more practical in the sense that it can be readily determined whether the person's teeth are adequately or evenly covered with the dental composition during treatment.

Comparative Study

A preformed dental tray similar to the tray depicted in FIG. 1 was made from ULDPE. The tray had a front and rear side wall thickness of 0.042 inch (1.08 mm) and a bottom wall thickness of 0.5 inch (1.27 mm). A number of such trays were heated in baths of boiling water having temperatures that ranged between 160–212° F. for a time period ranging from 3 to 20 seconds. In all cases the trays maintained sufficient physical integrity so that they could be successfully placed over a person's teeth and formed into a customized tray. The finished trays were soft, thin-walled, resilient, comfortable-fitting and virtually transparent.

By comparison, preformed trays made from EVA having a similar wall thickness were not able to maintain their physical integrity when heated in a similar manner. Instead, such trays tended to shrink and collapse in a manner that rendered them virtually useless. The front and rear side walls tended to collapse together, which made it virtually impossible to place over a person's teeth. They also shrunk and shriveled in a manner that substantially altered their initial size prior to being placed over a person's teeth, thereby further rendering them unsuitable for use in making a customized dental tray using a person's own teeth as a template. Studies have shown that preformed trays made from EVA must be significantly thicker-walled compared to preformed trays comprising ULDPE in order to perform with minimal adequacy. EVA trays having a wall thickness less than 1.5 mm have been found to be inadequate for formation of a customized dental tray using a person's teeth as a template without the use of an external support member, such as the outer tray disclosed in U.S. Pat. No. 5,616,027 to Jacobs et al. In general, EVA trays must typically have about twice the wall thickness as trays made from ULDPE in order to provide the same structural integrity when heated. This is yet another surprising and unexpected benefit of using preformed dental trays that comprise ULDPE.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of manufacturing a customized dental tray corresponding to a person's teeth comprising:
    providing a preformed tray comprising a bottom wall having a substantially U-shaped configuration, a front side wall extending laterally from an outer edge of the bottom wall, a rear side wall extending laterally from an inner edge of the bottom wall, and a hollow interior defined by the bottom wall, front side wall, and rear side wall that is sized and configured to approximate a corresponding shape of a person's dental arch, the front and rear side walls of the preformed tray having a thickness in a range of about 0.3 mm to about 1.8 mm;
    heating the preformed tray to a temperature at which said preformed tray becomes plastically deformable, the preformed being able to sufficiently retain its shape without external support so as to be useful in forming a dental impression;
    applying a blockout material to at least a portion of the person's teeth;
    upon applying the blockout material, placing the preformed tray over said at least a portion of the person's teeth without any external mechanical support other than fingers;
    causing the preformed tray to at least partially conform to the person's teeth in order to form a customized dental tray, wherein the blockout material forms one or more reservoirs within the interior of the customized dental tray;
    allowing the customized dental tray to cool to a temperature at which it is no longer plastically deformable;
    removing the customized dental tray from the person's teeth; and
    trimming the customized dental tray so that the tray does not significantly overlap the person's gingival when in use.

2. A method as defined in claim 1, the preformed tray being heated by immersing it in water.

3. A method as defined in claim 1, the preformed tray being heated by means of a heat gun or blow torch.

4. A method as defined in claim 1, the preformed tray being heated to a temperature in a range of about 110° to about 180° F.

5. A method as defined in claim 1, the preformed tray being heated to a temperature in a range of about 120° to about 170° F.

6. A method as defined in claim 1, the preformed tray being heated to a temperature in a range of about 130° to about 160° F.

7. A method as defined in claim 1, the preformed tray being caused to at least partially conform to the person's teeth by the person applying suction so as to remove at least one of air or water from between the person's teeth and the preformed tray.

8. A method as defined in claim 1, the preformed tray being caused to at least partially conform to the person's teeth by pressing the preformed tray against the person's teeth by means of at least one of a finger or the person's tongue.

9. A method as defined in claim 1, the blockout material comprising a curable resin.

10. A method as defined in claim 1, the preformed tray comprising ultra low density polyethylene.

11. A method as defined in claim 10, the preformed tray further comprising at least one of ethylene vinyl acetate, polycaprolactone, polypropylene or another form of polyethylene.

12. A method as defined in claim 1, the preformed tray further including a handle, the method further comprising removing the handle from the preformed tray and smoothing the customized dental tray in an area where the handle of the preformed tray was detached.

13. A method as defined in claim 1, the customized dental tray being trimmed so that an upper periphery of the customized dental tray terminates shy of the person's gingival margin when in use.

14. A method as defined in claim 13, further comprising scalloping the upper periphery of the customized dental tray up and around the person's interdental papilla.

15. A method as defined in claim 1, the preformed tray shrinking and more closely conforming to the person's teeth upon placing the tray over the person's teeth and allowing the tray to cool.

16. A method as defined in claim 1, the blackout material comprising a wax.

17. A method as defined in claim 1, the blockout material comprising at least one of a clay or putty.

18. A method of manufacturing a customized dental tray corresponding to a person's teeth comprising:
    providing a preformed sheet comprising a thermoplastic material;
    heating the preformed sheet to a temperature at which said preformed sheet becomes plastically deformable but is able to sufficiently retain its integrity as a sheet so as to be useful in forming a dental impression;
    applying a blockout material in at least a portion of the person's teeth;
    upon applying the blockout material, placing the preformed sheet over said at least a portion of the person's teeth without external support other than fingers;
    causing the preformed sheet to at least partially conform to the person's teeth in order to form a customized tray, wherein the blockout material forms one or more reservoirs within the interior of the customized dental tray;
    allowing the customized tray to cool to a temperature at which it is no longer plastically deformable;
    removing the customized tray from the person's teeth; and
    trimming excess tray material from the customized tray.

19. A method as defined in claim 18, the preformed sheet comprising ultra low density polyethylene.

20. A method as defined in claim 19, the preformed sheet further comprising at least one of ethylene vinyl acetate, polycaprolactone, polypropylene or another form of polyethylene.

21. A method as defined in claim 18, the preformed sheet having a rectangular or square shape.

22. A method as defined in claim 18, the preformed sheet having a horse-shoe shape.

23. A method as defined in claim 18, the preformed sheet being heated by immersing it in water.

24. A method as defined an claim 18, the preformed sheet being heated by means of a heat gun or blowtorch.

25. A method as defined in claim 18, the preformed sheet being heated to a temperature in a range of about 110° to about 180° F.

26. A method as defined in claim 18, the preformed sheet being heated to a temperature in a range of about 120° to about 170° F.

27. A method as defined in claim 18, the preformed sheet being heated to a temperature in a range of about 130° to about 160° F.

28. A method as defined in claim 18, the preformed sheet being caused to at least partially conform to a person's teeth by the person applying suction so as to remove at least one of air or water from between the person's teeth and the preformed sheet.

29. A method as defined in claim 18, the preformed sheet being caused to at least partially conform to the person's teeth by pressing the preformed sheet against the person's teeth by means of at least one of a finger or the person's tongue.

30. A method as defined in claim 18, the blockout material comprising a curable resin.

31. A method as defined in claim 18, the customized dental tray being trimmed so that an upper periphery of the customized dental tray terminates shy of the person's gingival margin when in use.

32. A method as defined in claim 31, further comprising scalloping the upper periphery of the customized dental tray up and around the person's interdental papilla.

33. A method as defined in claim 18, the preformed sheet shrinking and more closely conforming to the person's teeth after the tray has been formed, upon placing the tray over the person's teeth and allowing the tray to cool.

34. A method as defined in claim 18, the blockout material comprising a wax.

35. A method as defined in claim 18, the blockout material comprising at least one of a clay or putty.

* * * * *

UNITED STATES PATENT AND TRADEMARK OFFICE
CERTIFICATE OF CORRECTION

PATENT NO. : 6,848,905 B2
DATED : February 1, 2005
INVENTOR(S) : Scott Jacobs and Scot N. Andersen It is certified that error appears in the above-identified patent and that said Letters Patent is hereby corrected as shown below:

Column 2,
Line 21, change "controls" to -- control --.
Line 56, change "∈-polycaprolactone" to -- ε-polycaprolactone --.

Column 3,
Line 39, before "exposing" remove "other".

Column 8,
Lines 50 and 51, change "dray" to -- tray --.
Line 52, change "h eat" to -- heat --.

Column 10,
Line 9, after "portion of the teeth" insert -- , --.
Lines 28 and 29, change "trays wall" to -- tray walls --.
Line 51, change "0.5" to -- 0.05 --.

Column 11,
Line 39, before "being able to sufficiently" insert -- tray --.

Signed and Sealed this

Thirtieth Day of August, 2005

JON W. DUDAS
*Director of the United States Patent and Trademark Office*